US009186373B2

(12) United States Patent
Lametschwandtner et al.

(10) Patent No.: US 9,186,373 B2
(45) Date of Patent: Nov. 17, 2015

(54) SIRNA AGAINST CBL-B AND OPTIONALLY IL-2 AND IL-12 FOR USE IN THE TREATMENT OF CANCER (75) Inventors: Günther Lametschwandtner, Vienna (AT); Hans Loibner, Vienna (AT); Manfred Schuster, Schrick (AT); Isabella Haslinger, Vienna (AT); Sandra Seidl, Vienna (AT)

(73) Assignee: Apeiron Biologics AG, Vienna (AT)

( * ) Notice: Subject to any disclaimer, the term of this patent is extended or adjusted under 35 U.S.C. 154(b) by 0 days.

(21) Appl. No.: 13/977,453

(22) PCT Filed: Dec. 27, 2011

(86) PCT No.: PCT/EP2011/074099
§ 371 (c)(1),
(2), (4) Date: Aug. 1, 2013

(87) PCT Pub. No.: WO2012/089736
PCT Pub. Date: Jul. 5, 2012

(65) Prior Publication Data
US 2014/0010781 A1  Jan. 9, 2014

(30) Foreign Application Priority Data
Dec. 28, 2010  (EP) .................................. 10197146

(51) Int. Cl.
C07H 21/04    (2006.01)
A61K 31/713   (2006.01)
A61K 38/20    (2006.01)
C12N 15/113   (2010.01)
A61K 38/21    (2006.01)

(52) U.S. Cl.
CPC ............... *A61K 31/713* (2013.01); *A61K 38/20* (2013.01); *A61K 38/208* (2013.01); *A61K 38/2013* (2013.01); *A61K 38/212* (2013.01); *C12N 15/1137* (2013.01); *C12Y 603/02* (2013.01); *C12N 2310/14* (2013.01)

(58) Field of Classification Search
None
See application file for complete search history.

(56) References Cited

U.S. PATENT DOCUMENTS

| 2005/0037989 | A1  | 2/2005  | Lewis et al. ...................... 514/44  |
| 2006/0292119 | A1  | 12/2006 | Chen et al. ..................... 424/93.2 |
| 2007/0054055 | A1  | 3/2007  | Hsiao et al. .................... 427/372.2 |
| 2007/0054355 | A1  | 3/2007  | Reiss et al. .................... 435/69.1 |
| 2007/0087988 | A1  | 4/2007  | Sawasdikosol et al. .... 514/44 A |
| 2007/0178106 | A1* | 8/2007  | Romagne .................... 424/155.1 |
| 2007/0274915 | A1* | 11/2007 | Rao et al. ......................... 424/9.2 |
| 2010/0260808 | A1* | 10/2010 | Baier et al. ................... 424/277.1 |

FOREIGN PATENT DOCUMENTS

| WO | WO 2004/078130 | 9/2004 |
| WO | WO 2008/033403 | 3/2008 |
| WO | WO 2009/073905 | 6/2009 |
| WO | WO 2010/119061 | 10/2010 |

OTHER PUBLICATIONS

"Abstract for the 25th Annual Scientific Meeting of the International Society for Biological Therapy of Cancer", *Journal of Immunotherapy*, 33(8):859-920, 2010.
Ahlberg et al., "Stimulation of T-cell cytokine production and NK-cell function by IL-2, IFN-[alpha] and histamine treatment during remission of non-Hodgkin's lymphoma", *the Hematology Journal*, 4(5):336-341, 2003.
International Preliminary Report on Patentability issued in PCT Application No. PCT/EP2011/074099, mailed on Jul. 11, 2013.
International Search Report issued in PCT/EP2011/074099, mailed May 30, 2012.
Lametschwandtner et al., "Development of an Effective Cancer Immune Therapy by Cbl-b Silencing", *Journal of Immunotherapy*, 31(9):943, 2008.
Office Communication issued in European Application No. 10197146.3, dated Sep. 22, 2011.
Kojo et al., "Mechanisms of NKT cell anergy induction involve Cbl-b-promoted monoubiquitination of CARMA!", *Proceedings of the National Academy of Sciences of the United States of America*, 106(42):17847-17851, 2009.
Stromnes et al., "Abrogating Cbl-b in effector CD8+T cells improves the efficacy of adoptive therapy of leukemia in mice", *Journal of Clinical Investigation*, 120(10):3722-3734, 2010.
Various, "International Society for Biological Therapy of Cancer 23rd Annual Meeting Abstract", *Journal of Immunotherapy*, 31(9):921-971, 2008.
Weiss et al., "Immunotherapy of Cancer by IL-12-based cytokine combinations", *Expert Opinion on Biological Therapy*, 7(11):1705-1721, 2007.
Wigginton et al., "IL-12/IL-2 combination cytokine therapy for solid tumours : translation from bench to bedside", *Expert Opinion on Biological Therapy*, 2(5):513-524, 2002.
Ahmadzadeh, Mojgan et al., "Tumor antigen-specific CD8 T cells infiltrating the tumor express high levels of PD-1 and are functionally impaired," *Blood*, 2009(114):1537-1544, 2009.
Chiang et al., "Ablation of Cbl-b provides protection against transplanted and spontaneous tumors", *The Journal of Clinical Investigations*, 112(4):1029-1036, 2007.
De Paola et al., "Restored T-cell activation mechanisms in human tumour-infiltrating lymphocytes from melanomas and colorectal carcinomas after exposure to interleukin-2," *British Journal of Cancer*, 88(2):320-326, 2003.
Gladue, Ronald P. et al., "The CD40 agonist antibody CP-870,893 enhances dendritic cell and B-cell activity and promotes anti-tumor efficacy in SCID-hu mice," *Cancer Immunology, Immunotherapy*, 60:1009-1017, 2011.

(Continued)

*Primary Examiner* — Tracy Vivlemore
*Assistant Examiner* — Kate Poliakova
(74) *Attorney, Agent, or Firm* — Norton Rose Fulbright US LLP (57) ABSTRACT The invention relates to a method for the immune activation of NK cells by the reduction or inhibition of the Cbl-b function in said cells. This stimulates the congenital immune system and thus permits the therapy of appropriate diseases.

8 Claims, 5 Drawing Sheets (56) References Cited

OTHER PUBLICATIONS

Lametschwandtner et al., "Development of an effective cancer immune therapy by Cbl-b silencing," *J. Immuno.*, 31:943, 2008.

Loeser and Penninger, "The Ubiquitin E3 Ligase Cbl-b in T Cells Tolerance and Tumor Immunity," *Cell Cycle*, 6(20): 2478-2485, 2007.

Loeser et al., "Spontaneous tumor rejection by cbl-b-deficient $CD8^+$ T cells," *JEM*, 2007.

Ma, Daphne Y., and Clark, Edward A., "The role of CD40 and CD40L in Dendtritic Cells," *Seminars in Immunology*, 21(5): 265-272, Oct. 2009.

Mittendorf, "Evaluation of the CD107 cytotoxicity assay for the detection of cytolytic CD8+ cells recognizing HER2/neu vaccine peptides," *Breast Cancer Research and Treatment*, 92(1):85-93, 2005.

Morris et al., "Enhancing siRNA effects in T cells for adoptive immunotherapy", *Hematology*, 10(6):461-467, 2005.

Naramura et al., "c-Cbl and Cbl-b regulate T cell responsiveness by promoting ligand-induced TCR down modulation," *Nature Immunology*, 3(12): 1192-1199, 2002.

Parmiani et al., "Cytokines in cancer therapy," *Immunology Letters*, 74(1):41-44, 2000.

Rosenberg, "The emergence of modern cancer immunotherapy," *Annals of Surgical Oncology*, 12(5):1-3, 2005.

Schroder et al., "Interferon-gamma: an overview of signals, mechanisms and functions," *Journal of Leukocyte Biology*, 75(2):163-189, 2004.

Segura et al., "ICAM-1 on exosomes from mature dendritic cells is critical for efficient naive T-cell priming," *Blood*, 106(1):216-223, 2005.

Van Kooten and Banchereau, "CD40-CD40 ligand," *Journal of Leukocyte Biology*, 67:2-17, 2000.

Vonderheide and June, "A Translational Bridge to Cancer Immunotherapy", *Immunologic Research*, 27(2-3):341-355, 2003.

Yuan, Jianda et al., "CTLA-4 blockade enhances polyfunctional NY-ESO-1 specific T cell responses in metastatic melanoma patients with clinical benefit," *Proceedings of the National Academy of Sciences*, 105(51):20411-20415, 2008.

* cited by examiner

SEQUENCE LISTING

<160> NUMBER OF SEQ ID NOS: 8

<210> SEQ ID NO 1
<211> LENGTH: 21
<212> TYPE: RNA
<213> ORGANISM: Artificial Sequence
<220> FEATURE:
<223> OTHER INFORMATION: Synthetic siRNA

<400> SEQUENCE: 1
guacuggucc guuagcaaau u                                             21

<210> SEQ ID NO 2
<211> LENGTH: 21
<212> TYPE: RNA
<213> ORGANISM: Artificial Sequence
<220> FEATURE:
<223> OTHER INFORMATION: Synthetic siRNA

<400> SEQUENCE: 2
uuugcuaacg gaccaguacu u                                             21

<210> SEQ ID NO 3
<211> LENGTH: 21
<212> TYPE: RNA
<213> ORGANISM: Artificial Sequence
<220> FEATURE:

```
<223> OTHER INFORMATION: Synthetic siRNA

<400> SEQUENCE: 3
ggucgaauuu uggguauuau u                                              21

<210> SEQ ID NO 4
<211> LENGTH: 21
<212> TYPE: RNA
<213> ORGANISM: Artificial Sequence
<220> FEATURE:
<223> OTHER INFORMATION: Synthetic siRNA

<400> SEQUENCE: 4
uaauacccaa aauucgaccu u                                              21

<210> SEQ ID NO 5
<211> LENGTH: 17
<212> TYPE: RNA
<213> ORGANISM: Artificial Sequence
<220> FEATURE:
<223> OTHER INFORMATION: Synthetic siRNA

<400> SEQUENCE: 5
cucuauuugc ggaauua                                                   17

<210> SEQ ID NO 6
<211> LENGTH: 18
<212> TYPE: RNA
<213> ORGANISM: Artificial Sequence
<220> FEATURE:
<223> OTHER INFORMATION: Synthetic siRNA

<400> SEQUENCE: 6
cgagauaaaa cgccuuaa                                                  18

<210> SEQ ID NO 7
<211> LENGTH: 20
<212> TYPE: RNA
<213> ORGANISM: Artificial Sequence
<220> FEATURE:
<223> OTHER INFORMATION: Synthetic siRNA

<400> SEQUENCE: 7
gugagaauga guacuuuaaa                                                20

<210> SEQ ID NO 8
<211> LENGTH: 20
<212> TYPE: RNA
<213> ORGANISM: Artificial Sequence
<220> FEATURE:
<223> OTHER INFORMATION: Synthetic siRNA

<400> SEQUENCE: 8
uuagaauacu cauucucaca                                                20
```

SIRNA AGAINST CBL-B AND OPTIONALLY IL-2 AND IL-12 FOR USE IN THE TREATMENT OF CANCER

This application is a national phase application under 35 U.S.C. §371 of International Application No. PCT/EP2011/074099 filed 27 Dec. 2011, which claims priority to European Application No. 10197146.3 filed 28 Dec. 2010. The entire contents of each of the above-referenced disclosures is specifically incorporated herein by reference without disclaimer.

The present invention relates to therapeutic methods for activating the innate immune system, in particular NK cells.

NK cells (natural killer cells) pertain to the group of lymphocytes (a subtype of white blood cells or leukocytes). They are capable of recognizing and killing abnormal cells, such as tumor cells and virus-infected cells. NK cells do not have antigen-specific receptors and are a part of the innate immune system. NK cells recognize, i. a., the MHC I complex, which is found on virtually all healthy cells of the body. If a cell is infected by viruses or transforms into a tumor cell, the MHC I complex located on the cell surface may be lost. Like other lymphocytes, NK cells develop from lymphoid progenitor cells in the bone marrow and at a later stage circulate in the bloodstream.

Loeser et al. (JEM (2007) doi:10.1084/iem.20061699) have shown that Cbl-b is a negative regulator that is largely responsible for the so-called immunoreactivity of T cells. Cbl-b suppresses the activation of T cells and is capable of preventing autoimmune reactions. In the absence of Cbl-b, substances that are administered, but are hardly immunogenic, may lead to the induction of a strong immune response. Furthermore, Cbl-b-deficient mice (homozygous gene knockout) are viable and their immune system is capable of efficiently recognizing autologously induced tumors and establishing a lytic immune response thereto which is mainly based on $CD8^+$ T cells. However, the complete deactivation of the enzyme, as described in this document, also leads to an increase in autoimmunity after the immunization with superantigens.

Chiang et al. (Journal of Clinical Investigation 117 (4) (2007): 1033-1034) state that $Cbl-b^{-/-}CD8^+$ T cells can be used to enhance the anti-tumor reactivity in E.G7 mice.

Kojo et al. (PNAS 2009, 106 (42): 17847-17851) describe a mechanism that is influenced by Cbl-b in an artificially induced anergy of NKT cells.

WO 2008/033403 A describes the increase in reactivity of $CD8^+$ T cells by reducing the activity of Cbl-b. Inhibitory RNA sequences, in particular those from siRNA, directed against Cbl-b are disclosed.

WO 2009/073905 A2 describes an ex vivo treatment of cells of the immune system by means of Cbl-b inhibitors.

WO 2010/119061 A1 relates to methods for the intracellular determination of the expression of Cbl-b.

Lametschwandtner et al. (Journal of Immunotherapy 31 (9) (2008): 943) describe immunotherapies which are based on the suppression of Cbl-b in T cells.

Wigginton et al. (Expert Opinion on Biological Therapy 2002, 2 (5): 513-524) describe the infiltration of tumor tissue by $CD8^+$ T cells upon the administration of IL-12 and IL-2.

Weiss et al. (Expert Opinion on Biological Therapy, 2007, 7 (11): 1705-1721) describe various combinations of IL-12 and other cytokines as anticancer agents.

Lametschwandtner et al. (J. of Immunotherapy 2010, 33 (8): 899) describe immune-enhancing effects of IL-7.

Stromnes et al. (J. of Clinical Investigation 2010, 120 (10): 3722-3734) show that the administration of ex vivo expanded $Cbl-b^{-/-}CD8^+$ T cells in an adoptive immunotherapy in mice induces an anti-tumor response in vivo.

Thus it was already known that T-cells, i. e. cells of the adaptive immune system, may be activated by means of Cbl-b inhibition in order to promote an immune response. Such a promotion of the immune response is of therapeutic interest, in particular with respect to severe chronic diseases in which the insufficient activity of the immune system is causal for the progression of the disease. Such disorders are, for example, chronic infections or tumor diseases. However, in particular effective immune responses in these diseases require an efficient interaction of the adaptive and the innate immune system. However, no sufficient treatment approaches are clinically available yet, in particular with respect to the activation of NK cells.

It is therefore a primary object of the present invention to find new methods which are capable of providing a significantly improved efficiency of the immune response by activating the innate immune system, with particular reference to NK cells.

According to the present invention, this object has been achieved by the inhibition of Cbl-b in NK cells.

In a first aspect, the present invention relates a method for the immune activation of NK cells, comprising the step of reducing or inhibiting the function of Cbl-b in NK cells. This inhibition may be achieved by the administration of a Cbl-b inhibitor. Such an inhibitor may be directly administered to a patient in vivo.

In an equivalent related aspect, the present invention relates to a Cbl-b inhibitor for use in a method for the therapeutic treatment of a patient, comprising the introduction of the Cbl-b inhibitor into NK cells in the patient. By this treatment, the NK cells can be activated.

The terms "administration of a Cbl-b inhibitor" or "Cbl-b inhibition" are used interchangeably herein, in particular with respect to the description of specific embodiments.

The inhibition of Cbl-b according to the present invention can be used for immunotherapies in a patient, in particular for the activation of the immune system or the innate immune system, specifically mediated by NK cells. In particular, the method according to the present invention may be employed in the patient for the treatment of cancer, a viral infection, a bacterial infection, in particular a chronic infection, in particular a chronic infection with persistent intracellular bacteria, or a parasitic infection, in particular a mycosis. The therapy may be an immunotherapy of a chronic disease, including chronic infections. The infection may involve one or more organs, such as the liver. Preferably, the infection is a viral infection. One example is chronic hepatitis, e. g. triggered by a viral infection. The treatment of hepatitis B or hepatitis C is particularly preferred. The NK cell activation by the inhibition of Cbl-b according to the present invention is in particular effective in such diseases. The patient preferably is a mammal, in particular a human.

In particular in the case of cancer, the activation of NK cells according to the present invention may be combined with conventional therapies. Many tumor therapies, such as radiation therapy, chemotherapy or the surgical removal of tumors have been established for years and are constantly being refined and improved. New therapies comprise immunotherapies and therapies that are directed against specific markers of tumor cells, in particular with the use of monoclonal antibodies. Particularly the effect of the latter is largely dependent on the activity of NK cells that recognize the tumor cell-bound antibodies via general antibody determinants and consequently kill the tumor cell. The activation of the innate immune system via the effect of NK cells thus provides a further strategy that is able to complement and complete the already existing approaches in order to promote immune reactions on a broad scale, in particular for combating cancer cells. In particular, therapies that have a direct cytotoxic effect on tumor cells, such as chemotherapy or radiation therapy, are able to induce the expression of molecules of the MHC class and other immune-activating receptors, for example those of NKG2D ligands. These cellular changes are recognized by the cells of the innate immune system, in particular by NK cells, and lead to the activation thereof, by means of which it is possible to achieve a much stronger therapeutic effect owing to the synergy with the NK cell activation according to the present invention.

Accordingly, the cancer disease to be treated according to the present invention is preferably selected from cancer diseases of the reproductive organs, in particular ovarian cancer, testicular cancer, prostate cancer or breast cancer; cancer diseases of the digestive tract, in particular stomach cancer, colon cancer, rectal cancer, pancreatic cancer, esophageal cancer and liver cancer; kidney cancer, skin cancer, in particular melanoma, basal cell carcinoma and squamous cell carcinoma; neuroblastoma and glioblastoma, lung cancer, thyroid cancer, sarcoma, head and neck cancer, squamous cell carcinoma, lymphoma and leukemia (wherein the terms "cancer", "tumor", "carcinoma" etc. are always used interchangeably herein and refer to malignant diseases).

The Cbl-b gene and its gene products have been extensively described in the art (UniGene Id. Hs. 3144 and Hs. 381921). Cbl-b sequences are, e. g., publicly available in the GenBank database under the Acc. Nos. NM_008279 and NP_009112. Anti-Cbl-b antibodies, siRNAs and antisense inhibitors are commercially available. Specific siRNAs that are suitable for reducing or inhibiting the expression and thus the function of Cbl-b have been disclosed, for example, in document US 2007/0054355 in the form of mixed RNA/DNA nucleotides and having a length of about 20 bases.

Cbl-b inhibitors are well known in the prior art. According to the present invention, any Cbl-b inhibitor may be used. Preferably, the Cbl-b inhibitor is selected from inhibitory nucleic acids, in particular antisense oligonucleotides, in particular antisense RNA, siRNA (small interfering RNA) or shRNA (short hairpin RNA). Nucleic acid inhibitors can either be used as such or in the form of vectors which encode and express the inhibition. Suitable Cbl-b inhibitors are, for example, antagonists, aptamers or intramers, wherein the use of Cbl-b siRNA is preferred. siRNA technology for the attenuation of the specific gene expression has already been described for Cbl-b. Cbl-b inhibitors in accordance with the present invention are substances that reduce or inhibit the expression and/or function of Cbl-b and may either be identified as is known in the prior art (Loeser et al. (JEM (2007) doi:10.1084/iem.20061699; Chiang et al. (Journal of Clinical Investigation 117 (4) (2007): 1033-1034); Lametschwandtner et al. (Journal of Immunotherapy 31 (9) (2008): 943); Paolini et al. (J. Immunol. 2011 Feb. 15; 186 (4): 2138-47) or as described in the Examples of the present application.

US 2007/0087988 relates to a method for regulating HPK1, whose expression may be enhanced by increasing the expression of Cbl-b, and vice versa (e. g. by Cbl-b siRNA inhibition).

Preferably, the function of Cbl-b is reduced or inhibited by reducing or inhibiting the expression of Cbl-b. The terms "reduce/reduction" or "inhibit/inhibition" relate to a reduction or inhibition of the function (or expression) of Cbl-b as compared to the unmodified natural function, optionally including the complete inhibition of said function. Preferably, the function (or expression) is reduced by at least 30%, 40%, 50%, 60%, 70%, 80%, 90% or 95%.

In preferred embodiments of the present invention, the reduction or inhibition of the function of Cbl-b is transient, i. e. the function is only temporarily reduced as described in the above and can therefore recover again, e. g. by consumption or degradation of inhibitors, such as Cbl-b siRNA, or by restructuring or non-Cbl-b-impaired cells in vivo. The transient reduction of Cbl-b in immune cells can also be performed in a repetitive manner, e. g. until a therapeutic success has been achieved.

Preferably, the expression of Cbl-b is reduced or inhibited by the use of Cbl-b antisense RNA or siRNA. For this purpose, short DNA and/or RNA sequences that are complementary to one of the regions of the target (Cbl-b) mRNA sequence are employed, so that hybridization and inactivation of the corresponding sequences will occur. These sequences preferably have a length of at least 15, 18, 20, 22, 25, 28, 30, 35, 40, 50, 60, 70, 80, 90, 100, 120, 140, 160, 180 or up to 200 bases until the length of the complete target sequence is reached, preferably up to 2500, 2000, 1500, 1000, 500 or 300 bases. Preferably, the sequences of SEQ ID Nos. 1, 2, 3, 4, 5, 6, 7 and/or 8 are used.

The function of Cbl-b can also be reduced or inhibited by a plurality of other known components, e. g. by the use of Cbl-b antagonists, inhibitors, in particular aptamers or intramers. According to the present invention, any antagonists or inhibitors that are capable of suppressing the effect or function of Cbl-b can be used to enhance the immunoreactivity of NK cells. For the inhibition of Cbl-b, substances may be used that either specifically inhibit the enzymatic E3 ligase activity or inhibit the intracellular association of Cbl-b with its interaction partners or inhibit the expression of Cbl-b. Preferably, antagonists or inhibitors can be used for the preparation of a pharmaceutical agent for increasing the immunoreactivity of the NK cells according to the present invention. Treatments of diseases with a suppressed or inefficient immune system, in particular cancer or chronic infections, are facilitated.

According to the present invention it was found that the inhibition of Cbl-b together with further NK cell-stimulatory substances (NK cell activators) induces a synergistic effect that exceeds the effect that is to be expected based on the additive effects of the inhibition of Cbl-b and the activation of NK cells. Therefore, the administration of the Cbl-b inhibitor or the inhibition of Cbl-b is preferably carried out together with a further NK cell-stimulatory substance (NK cell activator). In the following, the terms "NK cell-stimulatory substance", "NK cell-activating substance" and "NK cell activator" are used interchangeably. Such an NK cell-stimulatory substance is a substance that differs from the Cbl-b inhibitor according to the present invention. An NK cell-stimulatory substance according to the present invention is a substance which induces the activation or stimulation of NK cells in one or more suitable in vitro assays. Preferably, the NK cell-stimulatory substance induces the production of IFN-gamma and/or TNF-alpha and/or the surface expression of CD107a by the NK cells in a manner independent of the inhibition of Cbl-b. Such production of IFN-gamma and/or TNF-alpha and/or surface expression of CD107a can be measured using methods known in the art (Fauriat Blood. 2010 Mar. 18; 115 (11): 2167-76; Dons'koi et al., J. Immunol. Methods 2011 Sep. 30; 372 (1-2): 187-95) or as is described in the Examples of the present application. Likewise, the effect of the NK cell-stimulatory agents may be tested by directly determining the cytotoxicity or "killing activity" of the NK cells (as described in Example 4; other suitable methods are well known in the art (Beano et al., J. Transl. Med. 2008 May 16;

6: 25; Claus et al., J. Immunol. Methods 2009 Feb. 28, 341 (1-2): 154-64; Fujisaki et al., Cancer Res. 2009 May 1, 69 (9): 4010-7; Cho et al., Clin. Cancer Res. 2010 Aug. 1, 16 (15): 3901-9), i. e. the cytotoxicity of NK cells and PBMCs, respectively, against specific target cells (SKBR3 tumor cells in Example 4) is determined, e. g. by measuring the release of the enzyme LDH from the tumor cell cytosol as a measure for the degree of cell lysis. In a corresponding in vitro measurement, the NK cells are preferably activated or stimulated in order to be able to measure the effect of the inhibition of Cbl-b, e. g. by contacting with tumor cells (e. g. K562) and/or by using a NK cell-stimulatory substance (e. g. one or more cytokines, such as IL-2 and/or IL-12) and/or an antibody (e. g. trastuzumab (Herceptin®)).

In a specific embodiment, the present invention relates to the co-administration of the Cbl-b inhibitor and an NK cell activator, in particular selected from an immune cell-stimulatory cytokine, e. g. a cytokine selected from the common gamma-chain cytokines, in particular IL-2, IL-15 and IL-21; cytokines that stimulate both the cells of the adaptive and of the innate immune system, in particular IL-12, IL-23 and IL-27; effector cell cytokines, such as IL-1, IL-17 and IL-18; an interferon, in particular interferon-alpha; or an interferon stimulator; an antibody, in particular an antibody which recognizes tumor cell surface molecules and/or an antibody whose constant region is capable of binding to the corresponding Fc receptor on NK cells; or a TLR or PAMP receptor ligand, in particular agonists, preferably of TLR-1, TLR-2, TLR-3, TLR-7, TLR-8 and TLR-9, as well as combinations of the above-mentioned NK cell activators. The terms "simultaneous" or "together with" or "in combination with" or "combined with" as used in the context of the administration of the substances according to the present invention refer to the administration of at least one Cbl-b inhibitor and at least one NK cell activator in a patient, which may be conducted in the form of one (containing at least one Cbl-b inhibitor and at least one NK cell activator) or more different pharmaceutical compositions (one of which contains at least one Cbl-b inhibitor and the other at least one NK cell activator and optionally other pharmaceutical compositions). If the administration is carried out using a plurality of different pharmaceutical compositions, the co-administration may be conducted simultaneously or sequentially. Particularly preferably, the administration of the Cbl-b inhibitor is carried out in combination with at least one NK cell activator, in particular IL-2, IL-15, IL-12, IL-23, interferon, an interferon stimulator, imiquimod and other TLR7/8 agonists, e. g. resiquimod, ssPolyU nucleotides, loxoribine, gardiquimod, CL075, CL097, CL264, 3M002, poly (I:C) oligonucleotides, CpG oligonucleotides, CD205 ligands or CD206 ligands, as well as combinations thereof. Preferred combinations of NK cell activators that may be combined with the administration of the Cbl-b inhibitor comprise, e. g., a cytokine of the common gamma-chain cytokines in combination with another of the above-mentioned NK cell activators; or a cytokine of the both the adaptive and the innate immune system in combination with another of the above-mentioned NK cell activators. Particularly preferred combinations are those involving a cytokine of the common gamma-chain cytokines and a cytokine of both the adaptive and the innate immune system, in particular IL-2 and IL-12.

According to the present invention, a cytokine of the common gamma-chain cytokines is selected from the family of cytokines that share the so-called common cytokine receptor gamma-chain ($\gamma_c$ or CD132) in their receptor complexes and consists of different members having a similar structure with four alpha-helical bundles. This family includes, e. g., interleukin (IL)-2, IL-4, IL-7, IL-9, IL-15, IL-21 and thymic stromal lymphopoietin (TSLP). An immune cell-stimulatory cytokine, a cytokine of both the adaptive and the innate immune system, an effector cell cytokine or an interferon stimulator according to the present invention are preferably selected from the group comprising IL-1, IL-2, IL-3, IL-4, IL-5, IL-6, IL-7, IL-8, IL-9, IL-11, IL-12, IL-13, IL-14, IL-15, IL-16, IL-17a, IL-17f, IL-18, IL-19, IL-20, IL-21, IL-22, IL-23, IL-24, IL-25, IL-26, IL-27, IL-28, IL-29, IL-30, IL-31, IL-32, IL-33, IL-34, IL-35, IFN-alpha, IFN-beta, IFN-gamma, IFN-lambda, TNF-alpha and TNF-beta.

In a particularly preferred embodiment, the present invention relates to the administration of a Cbl-b inhibitor in combination with IL-2, optionally with one or more further NK cell activators, in particular IL-12, IL-23, IFN-alpha and/or IFN-beta. In a further particularly preferred embodiment, the present invention relates to the administration of a Cbl-b inhibitor in combination with IFN-alpha, optionally with one or more further NK cell activators, in particular IL-15 and/or IL-21. In a further particularly preferred embodiment, the present invention relates to the administration of a Cbl-b inhibitor in combination with IL-12, optionally with one or more further NK cell activators, in particular IL-15 and/or IL-7.

Preferably, the NK cell-stimulatory substances used induce in NK cells the production of IFN-gamma and/or TNF-alpha and/or an increased surface expression of CD107a and/or an increased cytotoxicity against the target cells. IFN-alpha, IL-12 or IL-23, for instance, induce particularly strong IFN-gamma responses in NK cells. Surprisingly, it was now found that the activation of NK cells by the inhibition of Cbl-b with NK cell-stimulatory substances that induce the production of IFN-gamma evoke particularly strong synergistic effects that go far beyond the expected effect of the individual substances.

Likewise, the Cbl-b inhibitor may be administered in combination with an antibody, for example an antibody against tumor cell determinants, optionally combined with one or more of the above-mentioned immune activators or one or more of the above-mentioned NK cell-stimulatory substances. The inhibition of Cbl-b in NK cells as well as the administration of the additional NK cell activator or the antibody directed against tumor cells may be conducted in vivo, for example by direct administration to the patient.

Preferably, the Cbl-b inhibitor is coupled to a ligand of an NK cell recognition molecule, e. g. an NK cell surface molecule. Such a ligand can, for example, be a naturally occurring protein, a further biomolecule or a functional derivative thereof which is capable of binding to NK cells. In particular, such a ligand may be an antibody directed against an NK cell recognition molecule. According to the present invention, the NK cells are preferably specifically activated by the inhibition of Cbl-b in vivo, e. g. by coupling to a ligand of such an NK cell recognition molecule. The "specific" NK cell activation is to be understood as an effect on NK cells that is enhanced as compared to the non-specific, e. g. non-controlled or non-coupled, administration of a Cbl-b inhibitor, which may also have an effect in other cells. In particular, the "specific" NK cell activation is defined as an effect that is particularly directed to NK cells, as compared to the administration of a Cbl-b inhibitor alone (without the co-administration of an NK cell activator) or as compared to the administration of a Cbl-b inhibitor which is not coupled to a ligand of an NK cell recognition molecule. A nonspecific administration is carried out, e. g., by simple administration of the inhibitor without an additional administration of NK cell stimulators or NK cell-specific modifications of the inhibitor achieved by coupling to an NK cell recognition molecule. By means of the specific NK cell activation it is possible to control the NK cell-mediated immune response according to the present invention (innate immune system) with less undesired side effects which may, e. g., be caused by the adaptive immune system.

The term "antibody" relates to all naturally occurring antibodies, such as IgG, IgD, IgA, IgE and IgM antibodies as well as functional derivatives thereof which comprise, e. g., Fab, Fab', F(ab)$_2$, F(ab')$_2$ fragments, single-chain antibodies (scAb or scFv) or a fragment of an antibody variable domain, and which specifically bind to or are directed against an antigen, herein in particular an NK cell recognition molecule, or the corresponding Fc receptor on NK cells. Antibodies according to the present invention preferably have a constant region, in particular an Fc domain, which is capable of binding to the corresponding Fc receptor on NK cells. The antibody can be monoclonal or polyclonal. Antibodies which are to be administered within a therapy in combination with the Cbl-b inhibitor of the present invention, as described in the above, are directed against an epitope of a pathogen or a tumor and preferably have an Fc domain.

Among the preferred NK cell recognition molecules are, in particular, those which either specifically occur only on NK cells or which are particularly frequently expressed on NK cells and optionally on further additional immune cells whose activity can be enhanced as desired by Cbl-b inhibition, for example, CD2, CD8a, CD16, CD25, CD27, CD56, CD71, CD158, CD159, CD160, CD161, CD205, CD206, CD205, CD314, CD335, CD336 and CD337. Thus, the Cbl-b inhibitor can be contacted specifically with NK cells or with NK cells and further relevant subtypes of immune cells in a patient and can be taken up by the cells. Consequently, the Cbl-b inhibitor will exert its therapeutic effect only in the desired target cells in a specific manner.

In a further aspect, the present invention relates to a pharmaceutical composition comprising a Cbl-b inhibitor and an additional NK cell activator, as described above, in particular an immune cell-stimulatory cytokine, an interferon or an interferon stimulator, an antibody or a TLR or PAMP receptor ligand. Such a composition can be used for the above-mentioned purpose of inhibiting Cbl-b, either alone or in combination with further NK cell activators.

Preferably, the composition comprises a pharmaceutically acceptable carrier that is preferably suitable for the intracellular administration in a patient. In particular, the composition comprises vehicles such as liposomal or microsomal formulations which are particularly preferred for the administration of nucleic acids. Pharmaceutical compositions may comprise pharmaceutically suitable salts as well as additional buffers, tonicity components or pharmaceutically acceptable carriers. In particular, inhibitory nucleic acids, such as antisense nucleic acids, siRNA and shRNA, may be provided in suitable therapeutic vector systems. Pharmaceutical carrier substances are provided to improve the tolerability of the composition and to improve the solubility and bioavailability of the active ingredients. Examples include emulsifying agents, thickening agents, redox components, starch, alcohol solutions, polyethylene glycol or lipids. The selection of a suitable pharmaceutical carrier strongly depends on the mode of administration. For oral administration, liquid or solid carriers can be used, whereas final compositions in liquid form are advantageous for injections.

Preferably, the pharmaceutical composition to be used according to the present invention comprises buffer substances or tonic substances. By using a buffer, it is possible to adjust the pH value of the pharmaceutical composition to physiological conditions and to attenuate or buffer pH variations. An example for such a substance is a phosphate buffer. Tonicity agents are used to adjust the osmolarity and may comprise ionic substances, such as inorganic salts, e. g. NaCl, or non-ionic substances, e. g. glycerol, or carbohydrates.

Preferably, the composition to be used according to the present invention is provided to be suitable for a systemic, topical, oral or intranasal administration. These routes of administration of the pharmaceutical composition according to the present invention allow for a quick and easy intake. In case of an oral administration, it is, e. g., possible to ingest solid or liquid pharmaceutical compositions, either directly or in a diluted form.

The pharmaceutical composition to be used according to the present invention is preferably provided to be suitable for intravenous, intraarterial, intramuscular, intravascular, intraperitoneal or subcutaneous administration. For instance, injection or transfusions are suitable for this purpose. Administering the pharmaceutical composition directly into the bloodstream will have the advantage that the active ingredients of the pharmaceutical composition are distributed throughout the body and are thus capable of reaching their target tissues quickly. In addition, topical applications are provided. The administration either directly to or in the vicinity of a site at which an immune response is to be induced or enhanced, e. g. the site of an infection or a tumor, has the particular advantage that the NK cell activation will mainly occur at the target site.

In addition to the in vivo administration, an ex vivo treatment of NK cells is also possible. To this end, NK cells are isolated from a patient, treated ex vivo according to the present invention, subsequently activated and then returned to the patient. Such an ex vivo method for the treatment of cells of the immune system is, for example, described in WO 2009/073905 (incorporated herein by reference) and can be adapted to NK cells and used according to the present invention. Preferably, the ex vivo embodiment of the method according to the present invention is carried out in combination with the above-mentioned additional NK cell activators, such as immune cell-stimulatory cytokines, in particular IL-2 and/or IL-12, an interferon or interferon stimulator, an antibody or a TLR or PAMP receptor ligand, preferably of TLR-2, TLR-7 and TLR-8, as well as combinations thereof. It is possible that either the Cbl-b inhibitors or the additional NK cell activators are administered ex vivo to the NK cells and the further activation is carried out in vivo, e. g. ex vivo inhibition of Cbl-b and in vivo administration of the additional NK cell activator, or vice versa. Preferably, both steps, i. e. the inhibition of Cbl-b and the additional activation of NK cells, can be performed ex vivo. Isolated and activated NK cells can be administered to the target site in a directed manner. The NK cells can be isolated ex vivo. For a specific activation of NK cells, the NK cells may be enriched in a cell isolate, e. g. PBMCs, or be isolated therefrom ex vivo.

The ex vivo treatment of the NK cells may also include an expanding step, preferably as described in documents U.S. Pat. No. 7,435,596 B2 or WO 2006/52534 A2 (both incorporated herein by reference). In this context, for instance, NK cells can be contacted with NK cell-activating cells which express the MHC I complex only in a reduced manner and express membrane-bound IL-15. Alternatively or additionally, the NK cells can be contacted with IL-15 or an IL-15 receptor antibody and a CD137 ligand or a CD137 antibody. This expansion is optionally carried out in combination with said additional NK cell activators, such as immune cell-stimulatory cytokines.

The present invention is further illustrated by the following Figures and Examples, without being limited thereto.

EXAMPLE 1

Sequences

The following siRNA sequences were used for the inhibition of Cbl-b:

```
A. Sense sequence:
                                         (SEQ ID NO: 1)
GUACUGGUCCGUUAGCAAAUU Antisense sequence:
                                         (SEQ ID NO: 2)
5'PUUUGCUAACGGACCAGUACUU
```

```
B. Sense sequence:
                                         (SEQ ID NO: 3)
GGUCGAAUUUUGGGUAUUAUU Antisense sequence:
                                         (SEQ ID NO: 4)
5'PUAAUACCCAAAAUUCGACCUU
```

EXAMPLE 2

Cbl-b Inhibition in NK Cells

Figure 1:
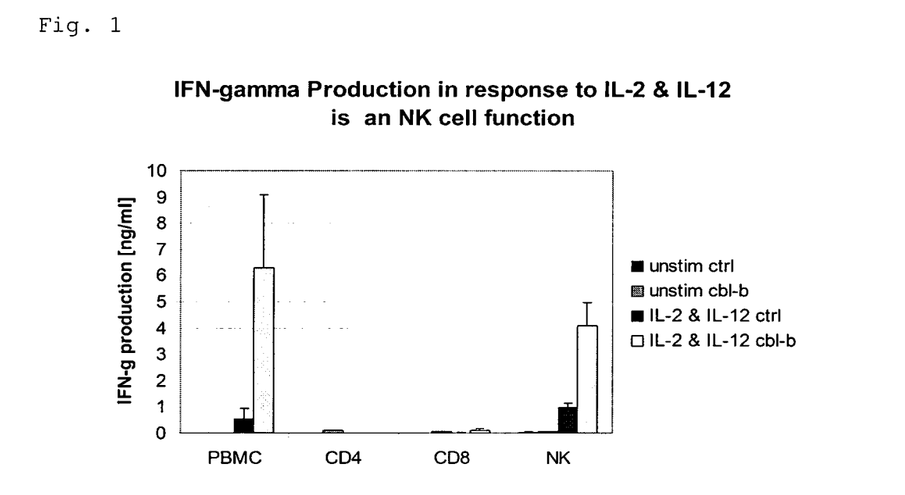
FIG. 1: PBMCs or cell fractions isolated therefrom were inhibited by Cbl-b siRNA and subsequently stimulated with IL-2 and IL-12, and the production of IFN-gamma was measured after 24 hours.

Using CPT reaction tubes (Vacutainer) whole blood was obtained from a donor and the PBMCs were separated therefrom by centrifugation. NK cells were isolated from PBMCs (including the $CD8^+CD3^-$ fraction) and subsequently CD8 and CD4 T cells were isolated by means of magnetic selection. FACS was used to verify that the purity of the corresponding cell populations was at least 90%. Both the PBMCs and the resulting isolated cell fractions were transfected with siRNA Cbl-b using an Amaxa transfection device and stimulated overnight with recombinant human IL-2 (50 ng/ml) and IL-12 (10 ng/ml) in Xvivo15 medium (FIG. 1). The IFN-gamma secretion in the cells treated in this manner was then measured in an ELISA. The result clearly indicates that the greatly enhanced IFN-gamma production of Cbl-b-inhibited PBMCs after the stimulation with IL-2 and IL-12 can be unambiguously assigned to the reaction of the NK cells.

EXAMPLE 3

Cbl-b Inhibition in NK Cells and Co-Stimulation

Figure 2:
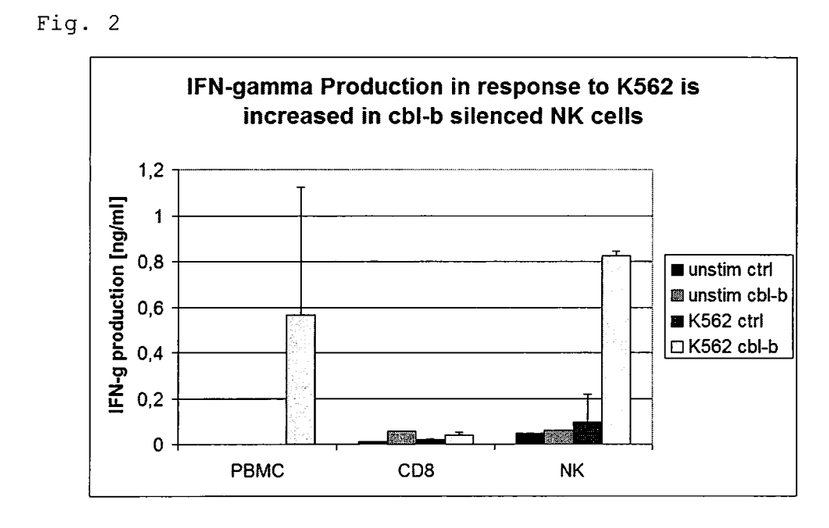
FIG. 2: PBMCs or cell fractions isolated therefrom were inhibited by Cbl-b siRNA, stimulated by co-incubation with the tumor cell line K562, and the production of IFN-gamma was measured after 24 hours.
Figure 3:
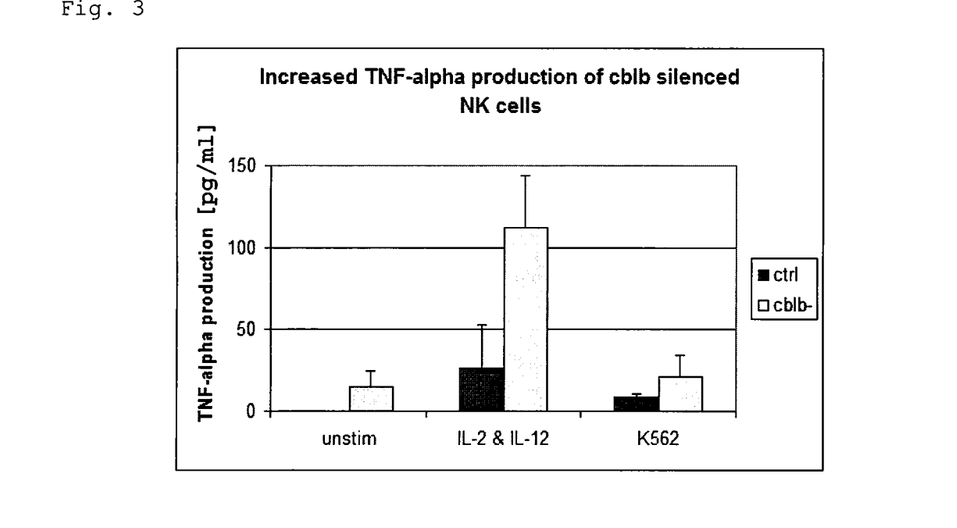
FIG. 3: Isolated NK cells were inhibited by Cbl-b siRNA, stimulated by K562 or IL-2 and IL-12, and the production of TNF-alpha was measured after 24 hours.

One possibility of co-stimulating NK cells is via tumor cell lines whose aberrant surface marker expression is no longer able to maintain the appropriate balance of inhibiting and activating NK receptors, thus leading to the activation of NK cells, for example the tumor cell line K562. PBMCs as well as CD8 and NK cells were isolated as described above and transfected with Cbl-b siRNA. $1\times10^5$ of these transfected cells were then incubated in Xvivo medium overnight, either alone (unstim) or with $6\times10^4$ of K562 tumor cells, and the secretion of IFN-gamma was determined as described above. The incubation of Cbl-b-inhibited PBMCs with this tumor cell line again resulted in a strong IFN-gamma production, which in turn could clearly be attributed to the contribution of the NK cells (FIG. 2). Furthermore, both stimulation methods resulted in an increase in the TNF-alpha production in NK cells upon inhibition by Cbl-b (FIG. 3).

EXAMPLE 4

Tumor Cytotoxicity by Cbl-b Inhibition in NK Cells

Figure 4:
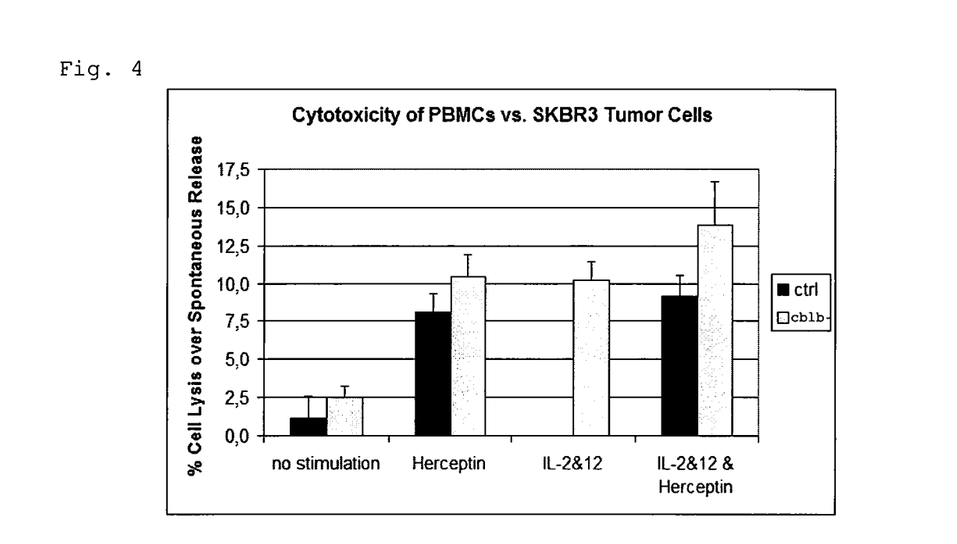
FIG. 4: PBMCs were inhibited with Cbl-b siRNA and incubated for 4 hours with the tumor cell line SKBR3, as indicated, with the addition of Herceptin or cytokine. The cytotoxicity was then determined based on the release of the cellular enzyme LDH which was measured in an enzymatic assay.

One of the main functions of NK cells in the context of tumor development is the direct destruction of tumor cells. It was therefore tested whether Cbl-b-inhibited PBMCs are better suitable for the destruction of tumor cells. The Her2-positive breast carcinoma line SKBR3 was used as a target cell line since in this context it is also possible to test the antibody directed against Her2 (trastuzumab or Herceptin) which is employed in tumor therapy. PBMCs were again isolated as described above, transfected with Cbl-b siRNA and incubated for 4 hours either alone or with $4\times10^4$ SKBR3 cells in Xvivo medium. In addition, 10 µg/ml of Herceptin antibody were added under the conditions indicated as Herceptin and in the conditions indicated as IL-2 IL-12 the stimulation was carried out as described above. The cytotoxicity of the PBMCs against the SKBR3 tumor cells was then determined by colorimetric measurement of the release of the enzyme LDH from the tumor cell cytosol. In accordance with the instructions given by the manufacturer of the colorimetric measurement kit (Biovision), the spontaneous release of this enzyme from the PBMCs or tumor cells was determined from the corresponding individual control conditions and was subtracted. It was found that the cell lysis induced by Cbl-b-inhibited immune cells was basically stronger than that obtained with the cells that had been treated with control siRNA, wherein, in particular, the simultaneous stimulation with IL-2 and IL-12 resulted in a significant increase in tumor cell lysis (FIG. 4).

These in vitro results therefore show that the simultaneous inhibition of Cbl-b in cells of the adaptive and the innate immune system ex vivo in unseparated human PBMCs is possible and further lead to the conclusion that the Cbl-b inhibition in NK cells forms a rational basis for combining Cbl-b inhibition with tumor therapies, such as the administration of recombinant IL-2 or therapeutic antibodies directed against tumor antigens.

EXAMPLE 5

Cbl-b Silencing in NK Cells Increases the Reactivity as Compared to IFN-alpha Stimulation NK cells contained in PBMC were isolated as described in Example 2 and were silenced using siRNA. The following siRNA sequences directed against Cbl-b were used:

```
Cbl-b siRNA 1:
                                 (SEQ ID NO: 5)
5'-CUCUAUUUGCGGAAUUA-3'

(SEQ ID NO. 6)
3'-AAUUCCGCAAAAUAGAGC-5'

Cbl-b siRNA 2:
                                 (SEQ ID NO: 7)
5'-GUGAGAAUGAGUACUUUAAA-3'

(SEQ ID NO: 8)
3'-ACACUCUUACUCAUAAGAUU-5'
```

Figure 5:
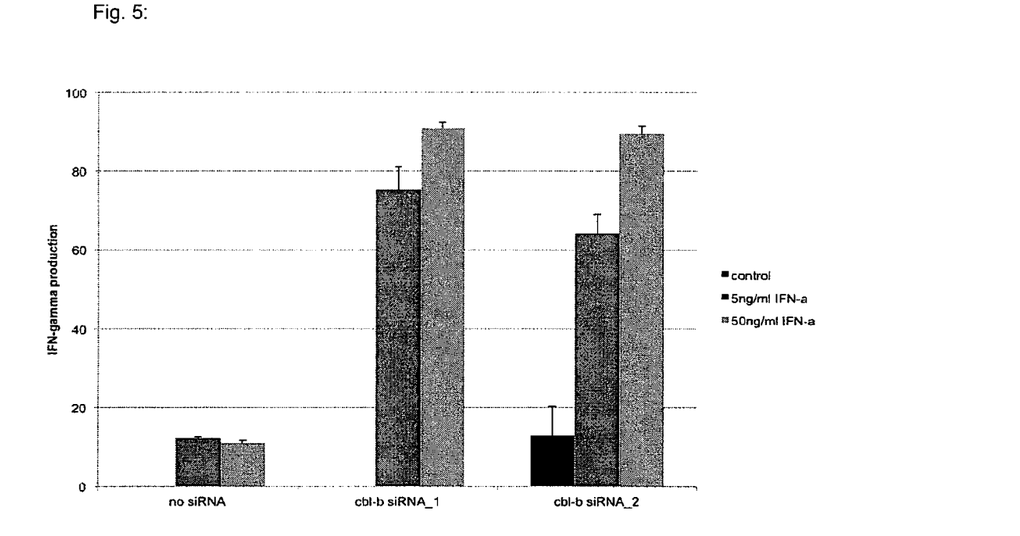
FIG. 5: Cbl-b silencing in NK cells increases the reactivity as compared to IFN-alpha stimulation: NK cells were inhibited by Cbl-b siRNA and stimulated with IFN-alpha and the production of IFN-gamma was measured after 24 h.

The cells were then stimulated overnight either without cytokine or with IFN-alpha (5 or 50 ng/ml, as indicated in FIG. 5) and the IFN-gamma secretion of the cells thus treated was then measured in an ELISA. The result clearly shows that the inhibition of Cbl-b in NK cells results in a strong increase in IFN-gamma production (FIG. 5). The IFN-gamma production of T and NK cells in the liver has been defined as one of the causal factors of the effectiveness of IFN-alpha therapy in the treatment of chronic hepatitis infections. This represents a basis for a rationale for a combination therapy with Cbl-b silencing and systemic IFN-alpha therapy, in particular in cases where the standard therapy with IFN-alpha alone is not sufficient to provide complete healing.

In principle, the liver is an ideal target organ for siRNA therapies as the gene expression in the liver can easily be modified by a systemic administration of siRNA. In the present case, both the Cbl-b inhibition in NK cells by direct systemic administration of Cbl-b siRNA and a cell therapy by transfer of NK cells that have been silenced ex vivo are thus possible since it is to be assumed that those cells migrate to the region of the affected liver in a sufficient amount after intravenous refunding

EXAMPLE 6

Cbl-b Silencing in NK Cells Increases the Reactivity as Compared to Combinations of IL-2 and IFN-alpha or IL-12/IL-23

Figure 6:
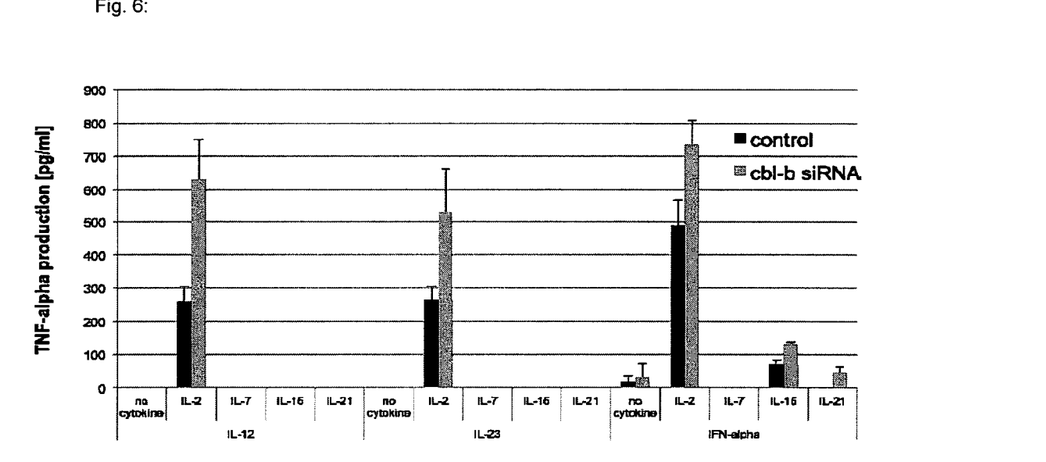
FIG. 6: Cbl-b silencing in NK cells increases the reactivity as compared to combinations of interleukins and IFN-alpha: NK cells were inhibited by Cbl-b siRNA and stimulated with IL-2, IL-7, IL-15 and IL-21, either alone or in combination with IL-12, IL- or IFN-alpha, and the production of TNF-alpha was measured after 24 h.

As it could be shown in Examples 2 and 5 that the inhibition of Cbl-b resulted in an increased stimulatability of NK cells by IFN-alpha and IL-2 and IL-12, respectively, a more systematic analysis of the stimulatability of Cbl-b-silenced NK cells was carried out. IL-2 is a member of the so-called common cytokine receptor gamma-chain family. Other members of this family include, i. a., IL-7, IL-15 and IL-21. IL-23 in turn is similar to IL-12 in various structural and functional aspects, just as IFN-alpha and IL-12, and is produced by activated dendritic cells, which thus also play an essential role in the activation of NK cells. Therefore, the NK cells in this experiment were stimulated with the common cytokine receptor gamma-chain cytokines IL-2, IL-7, IL-15 and IL-21, either alone or in combination with IL-12, IL-23 or IFN-alpha. For comparison, the DC cytokines IL--12, IL-23 and IFN-alpha were also added without common cytokine receptor gamma-chain cytokines. In this procedure, the NK cells contained in PBMCs were isolated as described in Example 5 and were silenced using siRNA (Cbl-b siRNA 2) and the control-treated and Cbl-b-silenced NK cells were directly compared. As indicated, the NK cells were stimulated with the cytokines overnight (all common cytokine receptor gamma-chain cytokines 50 ng/ml; DC cytokines IL-12, IL-23 and IFN-alpha 10 ng/ml). TNF-alpha was selected as a read-out (determined by ELISA) as TNF-alpha is a key cytokine in immune reactions and its production is not as dependent on IL-12 as that of IFN-gamma. The results in FIG. 6 show that the Cbl-b inhibition of NK cells leads to a significantly stronger activation and thus an increased production of TNF-alpha. The TNF-alpha production was particularly strong when the Cbl-b-silenced NK cells were costimulated with combinations of IL-2 and a DC cytokine, such as IL-12, IL-23 and IFN-alpha. However, it was shown that other common cytokine receptor gamma-chain cytokines, in particular IL-15 in the presence of IFN-alpha, resulted in a much stronger reaction of Cbl-b-silenced NK cells. Since the production of DC cytokines, such as IL-12, IL-23 and IFN-alpha, in vivo is mainly stimulated by components of pathogens acting as TLR ligands, a therapeutic rationale is therefore given to use the Cbl-b inhibition of NK cells either in case of chronic infections or in the therapy of tumor diseases with artificial TLR ligands (e. g. TLR7/8 ligands such as imiquimod or TLR9 ligands such as CpG). The additional stimulus provided by the common cytokine receptor gamma-chain cytokines IL-2 and IL-15 in vivo may be mediated, for example, by immunization with anti-tumor vaccines which lead to a production of IL-2 and IL-15 by activated antigen-specific T cells or by a direct therapeutic administration to the patient.

EXAMPLE 7

Figure 7:
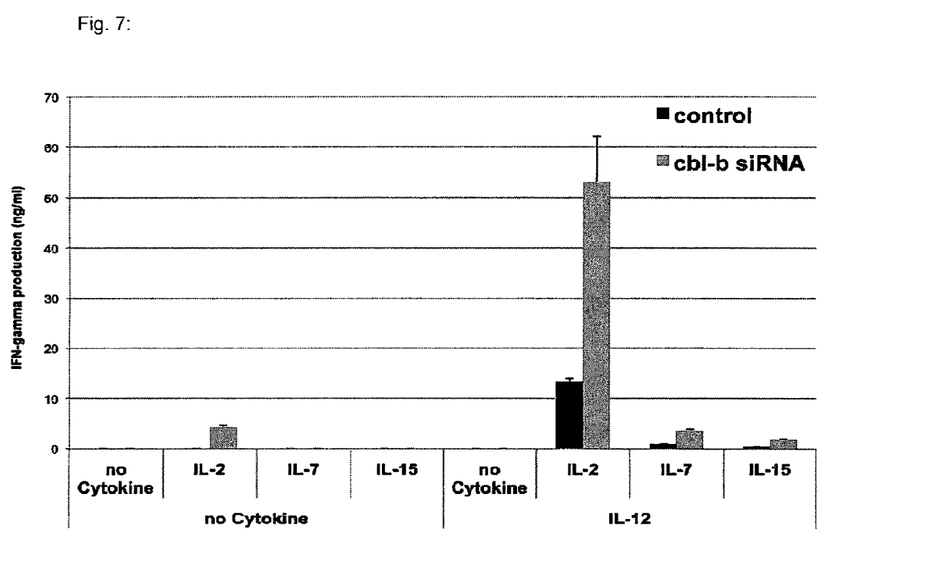
FIG. 7: Cbl-b silencing in NK cells increases the reactivity as compared to combinations of IL-12 with various cytokines of the common cytokine receptor gamma-chain cytokines: NK cells were inhibited by Cbl-b siRNA and stimulated with IL-2, IL-7 and IL-15, either alone or in combination with IL-12, and the production of IFN-gamma was measured after 24 h.

Cbl-b Silencing in NK Cells Increases the Reactivity as Compared to Combinations of IL-12 with Various Common Cytokine Receptor Gamma-Chain Cytokines As it could be shown in Example 6 that the inhibition of Cbl-b may result in an increased stimulatability of NK cells by various common cytokine receptor gamma-chain cytokines, in particular when used in combination with cytokines that are usually produced by DCs, it was tested whether, besides IL-2, IL-7 or IL-15 together with IL-12, the key factor for the induction of IFN-gamma, can also lead to an increased production of this cytokine. To this end, the NK cells contained in PBMCs were isolated as described in Example 5 and 6, silenced and stimulated overnight with the cytokines IL-2 (50 ng/ml), IL-7 and IL-15 (20 ng/ml each), either alone or in the presence of IL-12 (10 ng/ml), as indicated. The IFN-gamma production was measured in an ELISA. The results in FIG. 7 show that the Cbl-b-silenced NK cells are capable of a much stronger reaction in the form of IFN-gamma production in response to all three tested common cytokine receptor gamma-chain cytokines in the presence of IL-12. Likewise, it was found that only the Cbl-b-silenced NK cells were capable of a measurable production of IFN-gamma, solely based on the stimulation with IL-2. IL-2 has been approved for the treatment of certain malignant tumor diseases, but exerts a sufficient effect only a small subset of patients. The inhibition of Cbl-b in NK cells is thus in a potential strategy for improving the efficacy of IL-2 in tumor therapy. Furthermore, Cbl-b-silenced NK cells are capable of a substantially stronger response to the simultaneous presence of IL-12 and IL-7 or IL-15.

EXAMPLE 8

Figure 8:
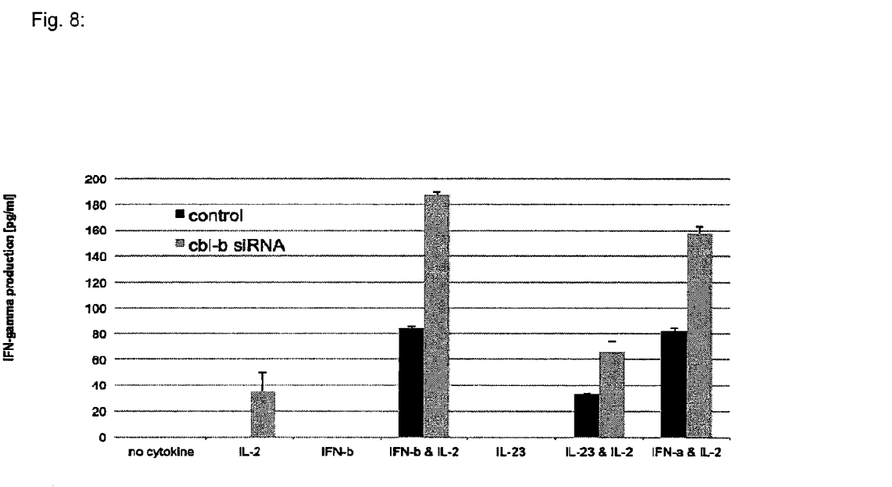
FIG. 8: Cbl-b silencing in NK cells increases the reactivity not only as compared to combinations of IL-2 with IL-12, IL-23 and IFN-alpha or IFN-beta: NK cells were inhibited by Cbl-b siRNA and stimulated with IL-23, IFN-alpha or IFN-beta, either alone or in the presence of IL-2, and the production of IFN-gamma was measured after 24 hours.

Cbl-b Silencing in NK Cells Increases the Reactivity not only as Compared to Combinations of IL-2 with IL-12, IL-23 and IFN-alpha, but also to IFN-beta As it was shown in Example 6 that the inhibition of Cbl-b in NK cells results in an increased stimulatability by IL-2 and IFN-alpha, it was also tested whether IFN-beta was capable of inducing an equivalent effect. To this end, the NK cells contained in PBMCs were isolated as described in Example 6, silenced and stimulated overnight with the cytokines IL-23, IFN-alpha or IFN-beta, either alone or in the presence of IL-2 (50 ng/ml) as indicated. The IFN-gamma production was measured in an ELISA. The results in FIG. 8 show that the Cbl-b-silenced NK cells are capable of a much stronger response in the form of IFN-gamma production to all three cytokines tested in the presence of IL-2.

EXAMPLE 9

Figure 9:
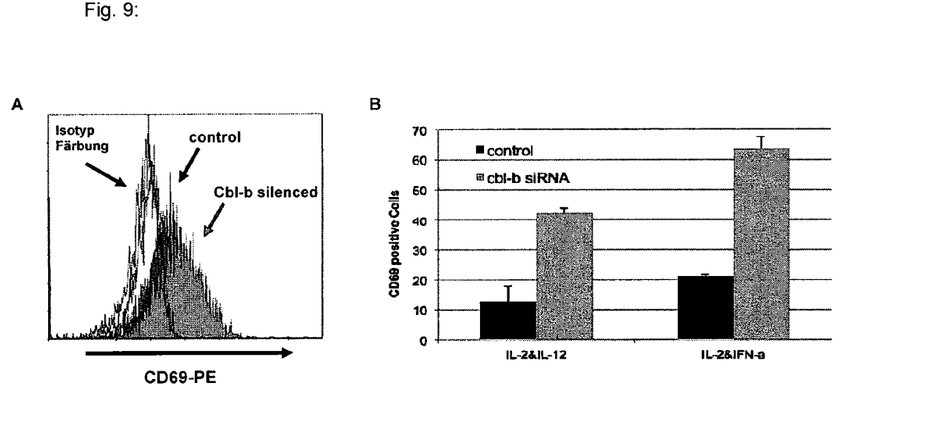
FIG. 9: The increased reactivity of NK cells subsequently to Cbl-b silencing as compared to cytokine stimulation leads to an increase of the activation marker CD69 on the cell surface: NK cells were inhibited by Cbl-b siRNA and stimulated with IL-2 and either IFN-alpha or IL-12, and the expression of CD69 was determined after 48 h.

The Increased Reactivity of NK Cells Upon Cbl-b Silencing as Compared to Cytokine Stimulation Leads to an Increase of the Activation Marker CD69 on the Cell Surface As it was shown in the previous examples that Cbl-b-silenced NK cells respond by increased cytokine production, the expression of the activation marker CD69 on the cell surface was examined as a further parameter using FACS. To this end, the NK cells contained in PBMCs were isolated as described in Example 6, silenced and stimulated with the cytokines IL-2 and IFN-alpha or IL-12. After 2 days, the cells were harvested and assayed for surface expression of CD69 by a FACS analysis conducted on an FC500 cytometer. For establishing the specificity of the staining, the cells were counter-stained using CD56-PE-Cy5 and CD3-FITC and stained with CD69-PE or a corresponding isotype control (the antibodies were routinely employed according to the recommended procedure given by the manufacturer Beckman-Coulter). As an example, FIG. 9A shows the increased expression of CD69 in Cbl-b-silenced NK cells as compared to control-treated NK cells, both of which were treated with IFN-alpha and IL-2, in the overlay-histogram. FIG. 9B summarizes the quantitative analysis of the CD69 expression for the stimulation with IL-2 and either IFN-alpha or IL-12. In accordance with the data obtained in the previous examples, it is shown that Cbl-b-silenced NK cells are hyper-reactive to a stimulation with these cytokines and that this increased reactivity directly manifests itself in the increased up-regulation of the activation marker CD69 on the cellular level.

The invention claimed is:

1. A method of treating cancer in a patient comprising administering at least one Cbl-b inhibitory nucleic acid further defined as an antisense oligonucleotide, siRNA, or shRNA, in combination with at least one NK cell-stimulatory substance further defined as at least one of the following combinations:

IL-2 and one or more of IL-12, IL-23, IFN-alpha, or IFN-beta, or any combination thereof; or IFN-alpha and one or both of IL-15 or IL-21; or IL-12 and one or both of IL-15 or IL-7.

2. The method of claim 1, wherein the Cbl-b inhibitor and at least one further NK cell-stimulatory substance is administered in combination with at least one of an immune cell-stimulatory cytokine, an interferon or interferon stimulator, an antibody having an Fc domain, or a TLR or PAMP receptor ligand.

3. The method of claim 1, wherein the Cbl-b inhibitor and at least one further NK cell-stimulatory substance is administered in combination with at least one of a cytokine of the common gamma-chain cytokine, a cytokine of both the adaptive and the innate immune system, an effector cell cytokine, a TLR receptor agonist, or a PAMP receptor agonist.

4. The method of claim 1, wherein the at least one Cbl-b inhibitor and the at least one further NK cell-stimulatory substance are comprised in one or more pharmaceutically acceptable carrier.

5. The method of claim 4, wherein the pharmaceutically acceptable carrier is suitable for intracellular administration in a patient.

6. The method of claim 5, wherein the pharmaceutically acceptable carrier is a liposomal or microsomal formulation.

7. The method of claim 1, wherein the patient is a mammal.

8. The method of claim 7, wherein the patient is a human.

* * * * *